(12) United States Patent
Kirakossian et al.

(10) Patent No.: US 7,927,561 B2
(45) Date of Patent: Apr. 19, 2011

(54) RAPID PARTICLE DETECTION ASSAY

(75) Inventors: Hrair Kirakossian, San Jose, CA (US);
Liping Yu, San Jose, CA (US); Douglas A. Petry, San Ramon, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 134 days.

(21) Appl. No.: 12/316,707

(22) Filed: Dec. 15, 2008

(65) Prior Publication Data
US 2009/0325192 A1     Dec. 31, 2009

Related U.S. Application Data

(60) Provisional application No. 61/010,686, filed on Jan. 10, 2008.

(51) Int. Cl.
*G01N 21/75*     (2006.01)
(52) U.S. Cl. .......... 422/402; 422/50; 422/400; 422/401; 436/518; 436/526; 436/164
(58) Field of Classification Search ............... 436/518, 436/524, 525, 526, 164; 422/50, 400, 401, 422/402
See application file for complete search history.

(56) References Cited

U.S. PATENT DOCUMENTS

| 4,115,535 | A |   | 9/1978  | Giaever |
|-----------|---|---|---------|---------|
| 4,731,337 | A |   | 3/1988  | Luotola et al. |
| 4,745,077 | A |   | 5/1988  | Holian et al. |
| 4,777,145 | A |   | 10/1988 | Luotola et al. |
| 5,236,824 | A | * | 8/1993  | Fujiwara et al. ................ 435/5 |
| 5,238,810 | A |   | 8/1993  | Fujiwara et al. |
| 5,238,815 | A | * | 8/1993  | Higo et al. ................... 435/7.92 |
| 5,252,493 | A |   | 10/1993 | Fujiwara et al. |
| 5,279,936 | A |   | 1/1994  | Vorpahl |
| 5,340,749 | A |   | 8/1994  | Fujiwara et al. |
| 5,374,531 | A |   | 12/1994 | Jensen |
| 5,445,970 | A |   | 8/1995  | Rohr |

(Continued)

FOREIGN PATENT DOCUMENTS
WO     WO 2007087582     8/2007

OTHER PUBLICATIONS

Lehmann, U. et al. "On-chip antibody handling and detection in a magnetic droplet manipulation system," 2B-2-Micro-and Nano-systems for Biology 1.

(Continued)

*Primary Examiner* — Melanie J Yu
(74) *Attorney, Agent, or Firm* — Douglas A. Petry

(57) ABSTRACT

The present invention proves instruments and methods for detecting and/or quantitating an analyte in a fluid sample. The fluid sample is placed in a sample chamber having a small, shallow detection region. The analyte is magnetically labeled using magnetic particles coated with a binding reagent, and is detectably labeled using a fluorescent dye or other detection reagent. The magnetically labeled analyte is concentrated into the detection region using a focusing magnet positioned underneath the sample chamber detection region. Concentrated analyte is measured using excitation optics positioned on top of the sample chamber detection region, adapted to illuminate only the detection region, and detection optics positioned on top of the detection region, adapted to detect only light emitted from the detection region. In a preferred embodiment, the invention provides a simple, rapid assay for measuring the concentration of $CD4^+T$ cells in a whole blood sample.

8 Claims, 13 Drawing Sheets

U.S. PATENT DOCUMENTS

| | | | |
|---|---|---|---|
| 5,476,796 | A | 12/1995 | Takahashi et al. |
| 5,498,550 | A | 3/1996 | Fujiwara et al. |
| 5,770,388 | A | 6/1998 | Vorpahl |
| 5,925,573 | A | 7/1999 | Colin et al. |
| 5,945,281 | A | 8/1999 | Prabhu |
| 5,985,153 | A | 11/1999 | Dolan et al. |
| 5,998,224 | A | 12/1999 | Rohr et al. |
| 6,136,549 | A * | 10/2000 | Feistel ............ 435/7.1 |
| 6,184,043 | B1 | 2/2001 | Fodstad et al. |
| 6,251,615 | B1 | 6/2001 | Oberhardt |
| 6,254,830 | B1 | 7/2001 | Pivarnik et al. |
| 6,258,607 | B1 | 7/2001 | Saito et al. |
| 6,265,229 | B1 | 7/2001 | Fodstad et al. |
| 6,294,342 | B1 | 9/2001 | Rohr et al. |
| 6,630,355 | B1 | 10/2003 | Pivarnik et al. |
| 6,645,777 | B1 | 11/2003 | Letcher et al. |
| 6,689,615 | B1 | 2/2004 | Murto et al. |
| 6,858,440 | B1 | 2/2005 | Letcher et al. |
| 2003/0049864 | A1 | 3/2003 | Nakamura et al. |
| 2006/0240572 | A1 | 10/2006 | Carron et al. |
| 2007/0117158 | A1 | 5/2007 | Coumans et al. |

OTHER PUBLICATIONS

Sha, M., et al. "Surface-Enhanced Raman Scattering Tags for Rapid and Homogeneous Detection of Circulationg Tumor Cells . . . ," Journal of the American Chemical Society (2008).

Mulvaney, S.P. et al. "Rapid, femtomolar bioassays in complex matrices combining microfluidics and magnetoelectronics," Biosensor Bioelectronics, Model BIOS-2431:1-10 (2007).

Ymeti, A., et al. "A Single Platform Image Cytometer for Resource-Poor Settings to Monitor Disease Progression in HIV Infection," Cytometry Part A, 71A: 132-142 (2007).

Pamme, N. "Magnetism and microfluidics," Lab Chip, vol. 6: 24-38 (2006).

Rodriguez, W., et al. "A Microchip CD4 Counting Method for HIV Monitoring in Resource-Poor Settings," PLoS Medicine, vol. 2, Issue 7: 0663-0672 (2005).

Gijs, M. "Magnetic bead handling on chip: new opportunities for analytical applications," Microfluid Nanofluid, vol. 1: 22-40 (2004).

Garth Rand, A. et al. "Optical Biosensors for Food Pathogen Detection," FoodTechnology, vol. 56, No. 3: 32-39 (2002).

Tibbe, A., et al. "Cell Analysis System Based on Compact Disk Technology," Cytometry, vol. 47: 173-182 (2002).

Tibbe, A., et al. "Cell Analysis System Based on Immunomagnetic Cell Selection and Alignment Followed by Immunofluorescent Analysis Using..," Cytometry, vol. 43: 31-27 (2001).

Carriere, D. et al. "Whole Blood Capcellia CD4/CD8 Immunoassay for Enumeration of CD4+ and CD8+ Peripheral T Lymphocytes," Clinical Chemistry, vol. 45, No. 1 :92-97 (1999).

MacCrindle, C., et al. "Particle Concentration Fluorescence Immunoassay: A New Immunoassay Technique for Quantifica-tion . . . ," Clinical Chemistry, vol. 31/9: 1487-1490 (1985).

* cited by examiner

RAPID PARTICLE DETECTION ASSAY

CROSS-REFERENCE TO RELATED APPLICATIONS

The present application claims priority to U.S. provisional application Ser. No. 61/010,686, filed Jan. 10, 2008, which is incorporated herein by reference in its entirety.

BACKGROUND OF THE INVENTION

1. Field of the Invention

The present invention relates in general to the fields of optical detection methods, immunology, and cellular biology, and, more particularly, to methods of assessing the state of the immune system, and, even more particularly, to methods of measuring $CD4^+$ T cells, as typically carried out in HIV-infected patients.

2. Description of Related Art

Obtaining accurate and reliable measures of $CD4^+$ T lymphocytes ($CD4^+$ T cells) is essential to assessing the immune system and managing the health care of persons infected with human immunodeficiency virus (HIV). The pathogenesis of acquired immunodeficiency syndrome (AIDS) is largely attributable to the decrease in $CD4^+$ T cells, and progressive depletion of $CD4^+$ T cells is indicative of an unfavorable prognosis.

In HIV-infected adults and adolescents, measurement of the number of $CD4^+$ T cells per volume of blood (referred to as the $CD4^+$ T cell count or simply the $CD4^+$ count, with the understanding that the measured quantity is a concentration) is used as a measure of disease progression and to establish decision points for initiating and monitoring antiretroviral therapy. The $CD4^+$ T cell count in infected patients decreases as HIV infection progresses, and patients with lower $CD4^+$ T cell counts have a poorer prognosis than patients with higher counts.

A wide variety of technologies have been used for measuring $CD4^+$ T cells. The most widely used assays for measuring $CD4^+$ T cells are based on flow cytometry. Cells of interest, e.g., $CD4^+$ T cells, in a sample are labeled with fluorescently labeled antibodies that bind specifically to cellular antigens whose joint expression identifies the cells of interest. The cells are passed in a fluid stream essentially one at a time through a detection region in which any fluorescent labels bound to a cell are optically detected. Cells of interest are identified by the joint detection of fluorescent labels bound to the cellular antigens whose joint expression identifies the cells of interest, and counted. Reagents and flow cytometers suitable for measuring $CD4^+$ T cells are commercially available from, for example, BD Biosciences (San Jose, Calif.).

Methods of counting the number of $CD4^+$ T cells in a sample using fluorescence microscopy have been described. Magnetic separation has been used to move the cells into position prior to analysis. For example, Tibbe et al., 2001, Cytometry 43:31-37, describe methods in which the $CD4^+$ T cells are magnetically separated into a detection region at the top of a sample chamber, the region is optically scanned to obtain an image of the region, individual cells are identified using image processing algorithms, and the number of $CD4^+$ T cells in the scanned region are counted. The requirements of scanning the sample add to the complexity and cost of the instrument. Assays based on identifying and counting cells of interest depend on the ability of the image processing to accurately identify the individual cells, and are sensitive to the density of the cells in the region.

Magnetic immunoassays have been described in which analyte-specific antibodies conjugated to magnetic particles are used to magnetically label a target analyte to facilitate magnetic separation of the analyte from the sample solution. Typically, after the magnetically labeled analyte has been concentrated against the side or bottom of the sample chamber, the sample fluid is removed. Such assays require sample handling fluidics to separate the captured analyte from the sample fluid and are inherently multi-step.

U.S. Pat. No. 5,945,281 describes a magnetic immunoassay in which a labeled target analyte is magnetically separated from a sample fluid and moved from a sample chamber into a detection region for optical analysis. The sample is added to sample chamber containing a magnetic capture reagents and a label such that target analyte in the sample forms a complex with the magnetic capture agent and the label. An electrical potential is applied to the complex to transport the complex to a detection region, and the presence of the complex in the detection region is determined.

U.S. Pat. Nos. 6,858,440; 6,645,777; 6,630,355; and 6,254,830; each incorporated herein by reference, describe a magnetic focusing immunosensor for magnetically concentrating pathogenic bacteria in a food sample onto the side of a sample container and optically detecting the concentrated cells through the side of the sample container. The magnetic focusing immunosensor comprises a focusing magnet and fiber optics attached to the side of the magnet for transmitting excitation and detection light.

BRIEF SUMMARY OF THE INVENTION

The present invention provides an optical instrument and method for the analysis of an analyte of interest in a fluid sample. The instrument enables measuring the total amount of analyte in the sample without the need to optically scan the sample. The assay is carried out in a "homogeneous" format in which the fluid sample is not removed from the sample chamber during the analysis. The invention provides significant advantages in simplicity and cost that will be particularly useful in applications such as the measurement of $CD4^+$ T cells.

Analysis of the fluid sample is carried out in a sample chamber shaped to minimize the background signal resulting from the sample fluid, which need not be removed from the sample chamber during the assay. The sample chamber includes a small detection region within the larger sample chamber, the detection region having a vertical depth preferably less than about 100 μm, more preferably less than about 50 μm, and even more preferably less than about 30 μm. The top of the sample chamber above the detection region is optically clear. The volume of the sample chamber preferably is less than about 100 μl, more preferably less than about 75 μl, and even more preferably less than about 50 μl. The sample chamber preferably is a shallow, flat sample chamber, more preferably approximately disk-shaped, with a depression in the top surface to decrease the vertical depth over the detection region.

The sample chamber can be made from any suitable material, such as glass or plastic. In a preferred embodiment, the sample chamber is made from plastic, such as polystyrene, has a clear (transparent) top to enable optical detection, and has black sides and bottom to minimize ambient or scattered light from interfering with the detection.

The instrument comprises a focusing magnet positioned under and adjacent to the detection region within the sample chamber, when the sample chamber is positioned in the instrument. The focusing magnet is magnetized in a vertical direction, and includes a tapered pole piece, preferably conical or frustum-shaped, that is tapered to less that about 100 μm, more preferably less than about 50 μm, and more preferably less than about 30 μm at the tip. In a preferred embodiment, the pole piece of the focusing magnet is conical. The pole piece may be an integral part of the magnet, or may be a separate piece made from a soft magnetic material in contact with the magnet.

The instrument further comprises excitation optics adapted to illuminate the detection region and detection optics adapted to measure light emitted from the detection region. The excitation and detection optics are positioned above the sample chamber, on the opposite side of the sample chamber from the focusing magnet. The positioning of the excitation and detection optics opposite from the focusing magnet enables uniform illumination of the magnetically concentrated analyte and detection of the emitted light from the analyte while the magnet remains in position and the analyte remains bound to the tip of the magnet, without interference from the magnet itself. In a preferred embodiment, a laser is used to provide excitation light, and a photodiode is used to measure the emitted light.

The methods of the invention comprise contacting a sample containing an analyte of interest with a capture reagent consisting of magnetic particles conjugated to a binding reagent specific for the analyte of interest, to obtain magnetically labeled analyte. The magnetically labeled analyte is further labeled with a detection reagent, such as a fluorescent dye, to enable optical detection. The sample is added to the sample chamber either prior to or subsequent to exposure to the capture and detection reagents. In one embodiment, the capture and/or detection reagents are present in the sample chamber, either in a liquid or dried form, at the time of sample addition. The sample chamber containing the sample mixed with the capture and detection reagents is positioned in the instrument, and the magnetically labeled analyte is magnetically concentrated into the detection region within the sample container using the focusing magnet positioned directly underneath the sample chamber. Without further separation of the analyte from the sample fluid (e.g., without aspirating the sample fluid or washing the concentrated sample), the amount of labeled analyte present in the detection region is then optically analyzed by illuminating the labeled analyte using the excitation optics and measuring the light emitted from the labeled analyte using the detection optics. The detection optics measure the light emitted from the detection region as a single measurement, without optical scanning over the detection region.

In a preferred embodiment of the invention, the capture reagent consists of a binding reagent attached to the magnetic particles, wherein the capture reagent is an antibody ("capture antibody") specific for the analyte of interest, or a component of the analyte. Preferably, the detection reagent consists of an antibody ("detector antibody") specific to a different epitope on the analyte of interest, or to a different component of the analyte, bound to a fluorescent dye. The magnetic particles coated with capture antibodies and the dye-labeled detector antibodies are added to the sample. If the analyte of interest is present, a magnetic complex is formed by the binding of the analyte to both the capture antibody and the detector antibodies. The magnetic complexes are attracted to the pole of the focusing magnet, and are thus concentrated in the detection region.

In preferred embodiments, the analyte of interest will be a cell from a bodily fluid, such as immune system cells of a cell type defined by the pattern of expression of one or more cell-surface molecules or antigens in a sample of whole blood. The magnetic capture and concentration of a cell is carried out using a magnetic particle-bound capture reagent that binds to a particular component of the cell, such as a cell-surface molecule. Detection of the captured cell is carried out using a detection reagent that binds to another cellular component, such as a cell-surface or intracellular molecule.

The capture reagent, bound to magnetic particle, preferably is an antibody that is specific to an antigen expressed on cells of the cell type of interest. As cell-surface antigens typically are expressed in high copy number, a cell can be bound simultaneously to a large number of antibody-coated magnetic particles. The force applied to the cell exposed to a magnetic field is the cumulative force applied to each of the bound magnetic particles, which is strong enough to concentrate the cells into the detection region.

In some embodiments, a single species of capture reagent is used, e.g., antibodies for a particular cell-surface antigen. In other embodiments, multiple species of capture reagents, each specific for a different cell-surface antigen expressed by the cells of interest, can be used to increase the number of magnetic particles that are bound to each cell and to increase the cumulative magnetic force applied to the cells during the concentration step.

Cells of the cell type of interest are labeled with a detection reagent, either before or after magnetic concentration, with a detection reagent to facilitate optical detection. The label can be bound indirectly to the cell using any suitable binding reagent, or can be bound directly to the cell. In a preferred embodiment, the detection reagent is an antibody specific for an antigen expressed on cells of the cell type of interest, conjugated to a fluorescent dye. Alternatively, a fluorescent dye that binds to a cell-surface or intracellular component may be used, such a membrane-specific dye or a nucleic acid binding dye.

In embodiments in which both the capture reagent and detector reagents are antibodies, the capture and detector antibodies are selected such that the simultaneous binding of both the capture and detector antibodies identifies the cells of interest. Such antibodies are referred to herein as cell subset-defining antibodies. The particular antibody pair should be selected in view of the other cell types potentially present in the sample. For example, if $CD4^+$ T cells are to be analyzed, the antibody pair should identify these cells in a sample also containing other blood cells, such as monocytes, granulocytes, B cells, NK cells, etc.

In a preferred embodiment, the present invention provides an instrument and method for quantitating $CD4^+$ T cells in a patient blood sample. The methods can be carried out in a whole blood sample, or in a sample of cells derived from whole blood, such as a sample of peripheral blood mononuclear cells ("PBMC"). The capture and detector antibodies are selected such that the simultaneous binding of both the capture and detector antibodies identifies $CD4^+$ T cells. Antibody pairs whose joint binding are sufficient to identify $CD4^+$ T cells, such as CD4/CD3 or CD4/CD45, are well known and have been described in the literature. Either antibody of the pair can be used for cellular capture, with the other being used to as the detector, although the overall assay performance may be improved using one of the two arrangements. The preferred pairing can be determined using routine experimentation.

In a preferred embodiment, the capture and detection antibodies are selected from the pair of CD3- and CD4-specific antibodies, one being used as the capture reagent and the other as the detection reagent. For example, the cells may be captured using CD4 antibody and labeled with CD3 antibody.

In another embodiment, a CD4-specific capture antibody is used to magnetically label the cells, and a fluorescent dye that binds to a cell structure, such a dye that binds DNA, is used to label the cells for optical detection. The specificity of the assay in this embodiment is dependent wholly on the specificity of the capture reagent; the detection reagent binds to all cells, captured or not. In particular, monocytes, which also express CD4, albeit to a lesser degree, may be captured and concentrated along with the $CD4^+$ T cells, will also become detectable labeled and will affect the total fluorescence measured. In this embodiment, it is beneficial to pretreat the sample prior to carrying out the assay to selectively remove monocytes, such as by magnetic depletion using CD14 antibody-coated magnetic particles. Reagents for the magnetic depletion of monocytes from a blood sample are commercially available from, for example, BD Biosciences (San Jose, Calif.).

The combination of features of the instrument of the present invention provides several advantages. The assays of the present invention is carried out without washing the sample after magnetic concentration, or otherwise separating the concentrated analyte from the sample fluid. The use of the focusing magnet enables concentration of the analyte sufficiently such that the amount of analyte can be detected without optically scanning the sample. The placement of the excitation and detection optics on the opposite side of the sample chamber from the focusing magnet facilitates optical detection in microliter-sized samples without physical interference from the focusing magnet, while the design of the sample chamber minimizes the amount of sample fluid in the excitation and detection light paths, thus reducing background signal caused by the presence of sample fluid in the light path.

Figure 1:
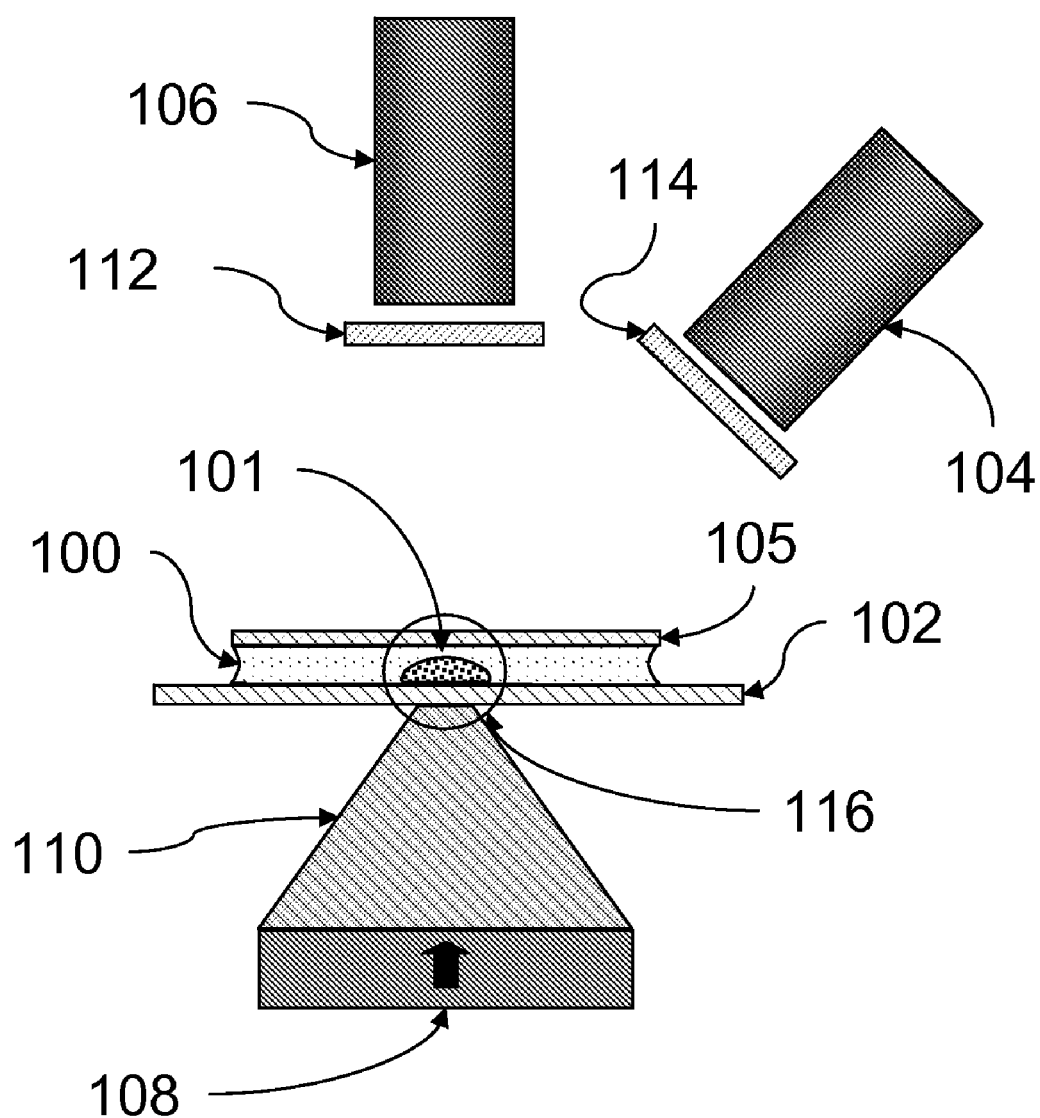
FIG. 1 shows an embodiment of the instrument of the present invention.

The figures that show elements of the instrument and sample chamber depict schematic representation of these elements and are not drawn to scale.

DETAILED DESCRIPTION OF THE INVENTION

In order that the invention herein described may be fully understood, a number of terms are explicitly defined, below. Terms not explicitly defined are intended to have their usual meaning in the fields of microscopy, cytometry, immunology, and HIV biology. Fluorescence imaging microscopy is described in, for example, Pawley (ed), Handbook of Biological Confocal Microscopy, 2nd Edition, Plenum Press (1989), and Murphy, 2001, "Fundamentals of Light Microscopy and Electronic Imaging" (Wiley-Liss, Inc. New York, N.Y.), both incorporated herein by reference. All reference cited herein, both supra and infra, are incorporated herein by reference.

By "whole blood" is intended a fluid blood sample as drawn in the presence of an anticoagulant from a mammal and substantially unfractionated thereafter.

The term "analyte" is used herein broadly to refer to any substance to be analyzed, detected, measured, or labeled. Examples of analytes include, but are not limited to, proteins, peptides, hormones, haptens, antigens, antibodies, receptors, enzymes, nucleic acids, polysaccharides, chemicals, polymers, pathogens, toxins, organic drugs, inorganic drugs, cells, tissues, microorganisms, viruses, bacteria, fungi, algae, parasites, allergens, pollutants, and combinations thereof. By convention, where cells of a given cell type are to be detected, both the cellular component molecules or the cell itself can be described as an analyte.

In preferred embodiments, the analyte of interest will be a cell of the immune system in a sample of whole blood, such as a $CD4^+$ T cell. It will be understood that the capture of a cell is carried out using a capture reagent that binds to a particular component of the cell, such as a cell-surface molecule, and detection of the captured cell is enabled using a detection reagent that binds to another cellular component, such as a cell-surface or intracellular molecule, and that both the cellular components and the cell itself can be described as an analyte.

As used herein an "analyte-specific reagent" or "target-specific reagent" broadly encompasses any reagent that preferentially binds to an analyte or target of interest, relative to other analytes potentially present in a sample. A target (analyte) and target-specific (analyte-specific) reagent are members of a binding pair, and either member of the pair can be used as the target-specific reagent in order to selectively bind to the other member of the pair. Examples of target and target-specific reagent pairs include, but are not limited to, antigen and antigen-specific antibody; hormone and hormone receptor; hapten and anti-hapten; biotin and avidin or streptavidin; enzyme and enzyme cofactor; lectin and specific carbohydrate; and complementary nucleic acid sequences. Preferred target-specific reagents are antibodies that include an antigen binding site that specifically binds (immunoreacts with) an antigen.

"Antibody", as used herein, includes all products, derived or derivable from antibodies or from antibody genes, that are useful as target-specific binding reagents in the cytometric methods described herein. "Antibody" thus includes, inter alia, natural antibodies, antibody fragments, antibody derivatives, and genetically-engineered antibodies, antibody fragments, and antibody derivatives.

"Cell subset-defining antibody" refers to any antibody that may be used, alone or in combination with other antibodies, to facilitate identification of a particular subset of cells, and thus includes antibodies that are specific for epitopes displayed by cells of the subset. Typically, cell subsets may be identified by the presence of particular markers expressed by the cell and/or the absence of particular markers. By "absence" is intended a level of expression, as measured in an immunoassay, such as a cytometric assay, that is not significantly different from background.

As used herein, "magnetic particles" refers to any particle that contains a magnetic or magnetically responsive material. Magnetic particles can be of any shape, but typically are approximately spherical ("microspheres"). Magnetic particles suitable for use in the present invention preferably have a diameter in the nanometer to micrometer range, typically about 0.01 to 50 µm in diameter, preferably about 0.1 to 10 µm, more preferably about 0.2 to 0.4 µm. Preferably, the magnetic particles are paramagnetic or superparamagnetic. Magnetic particles suitable for use in the present invention are commercially available from a number of sources, including, but not limited to, BD Biosciences (San Jose, Calif.), Invitrogen (Carlsbad, Calif.), Miltenyi Biotech (Bergisch Gladbach, Germany), and Polysciences (Warrington, Pa.).

Magnet Capture Reagent

The magnetic capture reagents are magnetic particles bound to one or more target-specific reagents. Preferred target-specific reagents are antibodies. Magnetic particles coated with antibodies specific for various cell-surface molecules, such as CD4 or CD3, are commercially available from a number of sources, including, but not limited to, BD Biosciences (San Jose, Calif.), Invitrogen (Carlsbad, Calif.), and Miltenyi Biotech (Bergisch Gladbach, Germany). In general, antibody-coated magnetic particles sold for use in cell separation assays are suitable for use in the present invention.

Detection Reagent

A detection reagent is used to enable optical detection of the magnetically concentrated analyte. In many embodiments, the detection reagent comprises, or is, a fluorescent dye. In general, fluorescent dyes (fluorophores) suitable for use in the present invention can be selected from any of the many dyes suitable for use in imaging applications. However, the invention is not limited to the use of fluorescent dyes, and any of the detection reagents useful in fluorescence microscopy that bind to the analyte of interest and enable optical detection, such as nanoparticles detectable by surface-enhanced raman scattering (SERS), may be used.

The detection reagent may comprise an analyte-specific reagent labeled with a detectable label, such as a fluorescent dye or dye-containing particle. Fluorescent dyes are known to those of skill in the art and are commercially available from a number of sources. Suitable fluorescent dyes include, but are not limited to, phycoerythrin ("PE"), fluorescein isothiocyanate ("FITC"), allophycocyanin ("APC"), Texas Red ("TR", Molecular Probes, Inc.), peridinin chlorophyll complex ("PerCp"), CY5 (Biological Detection System) and conjugates thereof coupled to PE (e.g., PE/CY5, PE/APC and PE/TR); etc. A large number of dyes are commercially available from a variety of sources, such as, for example, Molecular Probes (Eugene, Oreg.) and Exciton (Dayton, Ohio).

Where the analyte-specific reagent is an antibody, the antibodies can be directly conjugated to a fluorescent label or can be labeled indirectly using a secondary antibody (e.g., a goat anti-mouse antibody conjugated directly to a fluorescent label) or by conjugating the antibody to one member of a binding pair (e.g., biotin) and using a dye conjugated to the other member of the binding pair (e.g., avidin or streptavidin). Direct conjugation is preferred, however, in many embodiments. A wide variety of fluorescently labeled antibodies suitable for use in the present invention are commercially available from, for example, BD Biosciences (San Jose, Calif.).

Alternatively, particularly for the detection of cells, the detection reagent may consist of a fluorescent compound that binds to a cellular component, either on the cell surface or intracellular. In a preferred embodiment, the detection reagent is a "permeant dye" that is a light emitting compound capable of permeating cell membrane walls and binding to an intracellular molecule. Preferably, the permeant dye is a fluorescent nucleic acid binding compound.

Permeant dyes are known to those of skill in the art. Preferred permeant dyes are permeant fluorescent nucleic acid binding compounds that exhibit an increase in fluorescence upon binding to nucleic acid, such as, for example, thiazole orange and analogs thereof (such as those described in U.S. Pat. Nos. 4,883,867; 4,957,870; 5,656,449; each incorporated herein by reference); anthraquinone and derivatives thereof (such as DRAQ5™ and others described in U.S. Pat. No. 6,468,753, incorporated herein by reference); and SYTO® dyes (described in U.S. Pat. Nos.: 5,436,134 and 5,534,416, both incorporated herein by reference), available from Molecular Probes (Eugene, Oreg.). Other useful permeant dyes include 4',6-diamidino-2-phenylindole (DAPI) and Hoechst stains.

Focusing Magnet

Magnetic concentration of magnetic particles is carried out using a focusing magnet that has a tapered pole piece to concentrate the magnetic flux. The tapered pole piece preferably is conical or frustum-shaped. The focusing magnet preferably consists of a permanent magnet, typically a rare-earth magnet (e.g., neodymium or samarium-cobalt), which has its remnant magnetization perpendicular to the top and bottom surfaces, and a conical or frustum-shaped magnetic pole piece made from soft magnetic material, such as, for example, iron, positioned on the top of magnet. Alternatively, the focusing magnet can be a one-piece conical or frustum-shaped permanent magnet, magnetized in a direction parallel to the axis of the cone.

Alternatively, the focusing magnet can be an electromagnet consisting of a wire coil surrounding a core of a soft magnetic material, wherein the core as a conical or frustum-shaped end.

The focusing magnet preferably concentrates the magnetic particles in the sample into a pellet. The size and shape of the pellet will be determined by the number and type of particles added to the sample, which will depend on the application, the size of the tip of the focusing magnet, and the distance of the tip from the focusing magnet to the pellet, which will depend on the thickness of the bottom of the sample holder. The magnetic particles are drawn to the tip of a conical focusing magnet. For a frustum-shaped magnet, the particles are drawn to the edge of the tip of the focusing magnet, and are concentrated in a ring corresponding to the diameter of the tip. The size of the tip of the focusing magnet preferably is no bigger than the expected size of the pellet so that the particles are concentrated into a single pellet. For $CD4^+$ T cell assays, as described in the examples, the concentrated pellet of magnetic particles and magnetically labeled cells is typically about 500 µm to 1 mm in diameter.

DESCRIPTION BASED ON THE FIGURES

While this invention is satisfied by embodiments in many different forms, shown in the drawings and described herein in detail are preferred embodiments of the invention, with the understanding that the present disclosure is to be considered as exemplary of the principles of the invention and is not intended to limit the invention to the embodiments illustrated.
FIG. 1

FIG. 1 shows an embodiment of an instrument of the present invention. The instrument comprises a flat sample holder 102 that holds the sample 100 containing magnetic particles bound to an analyte, such as cells or molecules. An optically transmissive cover slip 105 is placed on top of the sample to decrease and make uniform the depth of the sample.

The cover slip, preferably made of glass, is placed over the sample fluid such that the sample fluid will spread to fill the space between the cover slip and the sample holder. The size of the cover slip is selected based on the volume of sample used to provide a uniform depth of sample of the desired dimension. The shape of the cover slip is not critical, and standard rectangular cover slips used in microscopy are suitable.

The instrument further comprises a focusing magnet adapted to concentrate magnetic particles present in the sample into a pellet 101 within a detection region 116. The focusing magnet consists of a permanent magnet 108, which has its remnant magnetization perpendicular to the top and bottom surfaces (indicated by the arrow), and a conical or frustum-shaped magnetic pole piece 110, made from soft magnetic material, such as, for example, iron, is positioned on the top of magnet 108. The pole piece 110 concentrates the magnetic flux from magnet 108 and produces a high gradient magnetic field, with the highest flux density at the top. In order to obtain the highest magnetic field amplitude and gradient in the sample, the pole piece 110 is positioned below sample holder 102 such that the top of the pole piece is adjacent to, or touching, the bottom of sample holder 102. The thickness of sample holder 102 preferably is minimized, while maintaining structural integrity. Preferably, the thickness of sample holder 102 is approximately 0.15 to 0.2 mm.

The instrument further comprises an illumination light source 104, preferably a laser, adapted to provide illumination light onto detection region 116 that encompasses the region into which the magnetic particles are concentrated. The illumination light source may contain optics 114 that focus or shape the illumination beam to limit the region illuminated to the detection region. In a preferred embodiment, optics 114 is a simple pin-hole device. Illumination light source 104 can also include a frequency-dependent filter (not separately shown), such as band-pass filter or a short-pass filter, to select the range of wavelengths that impinge on the sample.

The instrument further comprises a detector 106, adapted to detect light emitted from detection region 116. The detector may contain detector optics 112 that focus the light on the detector and to limit the area from which emitted light is detected to the detection region 116. In a preferred embodiment, a simple pin-hole device is used to limit the area from which emitted light is detected to the detection region 116. The detector optics further include a frequency-dependent filter, such as band-pass filter or long-pass filter is used to reduce the amount of scattered excitation light entering the detector.

Light emitted from labeled analyte bound to the magnetic particles concentrated into the detection region 116 is detected by detector 106, which produces an electrical signal that is a function of the total amount of light measured from the detection region 116. In a preferred embodiment, detector 106 is a photodiode. However, other optical detectors, such as a photomultiplier tube (PMT), avalanche photodiode (APD), or CCD camera, can be adapted for use in the present instrument to detect the total amount of light emitted from detection region 116.

The concentration of the analyte-bound particles into a pellet 101 with a volume much smaller than the volume of the sample 100 effectively separates the analyte of interest from the majority of the medium and enables measuring the fluorescence from the pellet largely free of the background signal generated from other components of the sample. Additional features of the instrument further reduce the background signal observed. The illumination optics are adapted to illuminate only detection region 116. The detection optics are adapted to measure light emanating essentially only from the detection region 116. The detection optics further are adapted to measure light that emitted from the detection region in a light path essentially perpendicular to the plane of the sample holder, which minimized the amount of sample the light passes through before exiting the sample. Each of these features functions to minimize the contribution to the total fluorescence caused by components in the sample.

In preferred embodiment, a precisely measured volume of sample 100 is provided, which facilitates obtaining a quantitative measurement of the concentration of analyte in the sample. However, a qualitative measurement can be obtained without control over the sample volume. For example, a diagnostic assay in which it is sufficient to detect the presence of analyte in the sample can be carried out using a sample having a less precisely measured volume.

FIG. 2

Figure 2:
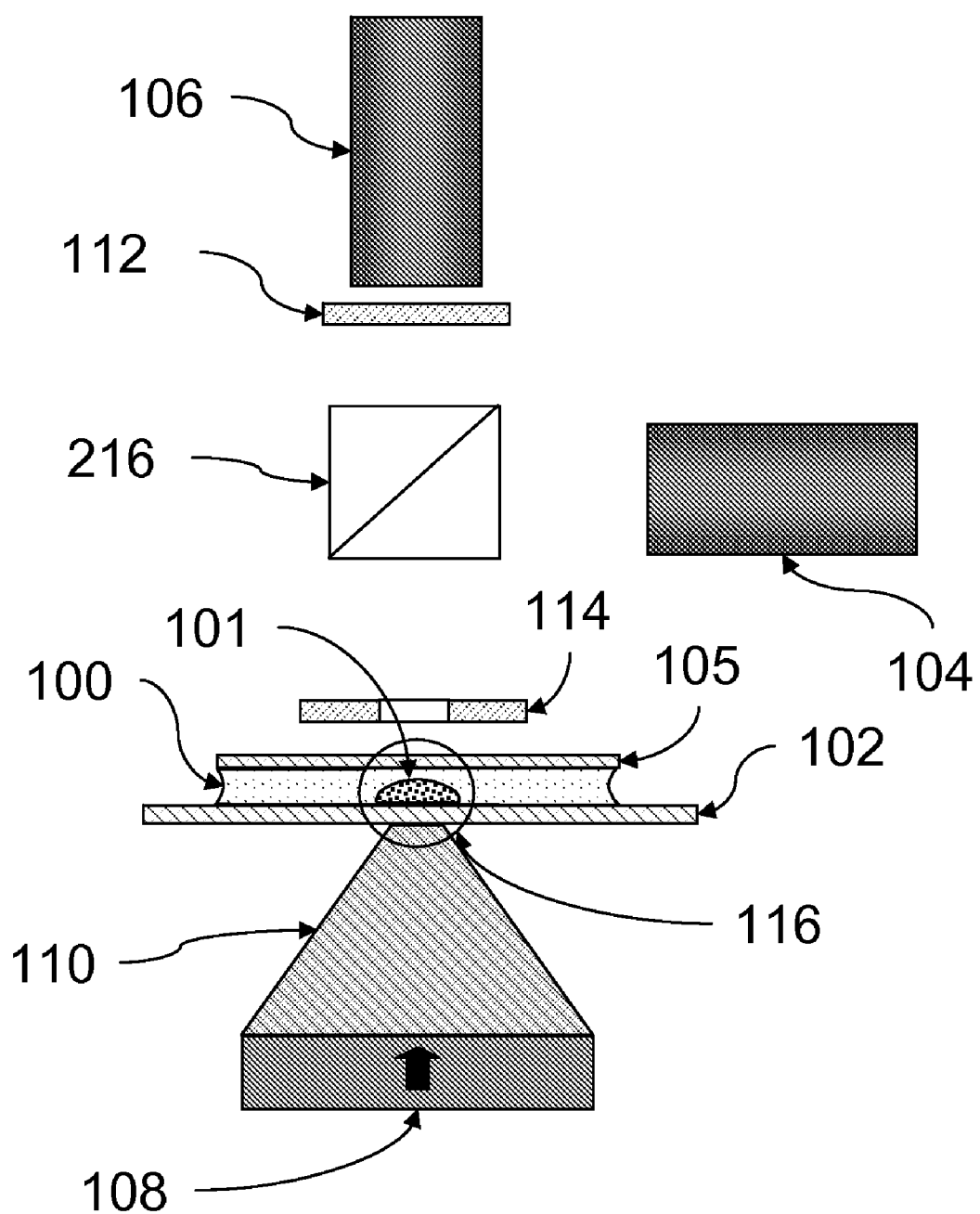
FIG. 2 shows an alternative embodiment of the instrument of the present invention.

FIG. 2 shows an alternative embodiment of the instrument of the present invention incorporating a standard epifluorescence light path. Beam splitter 216 contains a dichroic mirror which reflects the excitation light from light source 104 towards the detection region 116. Light emitted from the fluorescent labels in the sample passed through the beam splitter towards detector 106.

FIG. 3

Figure 3A:
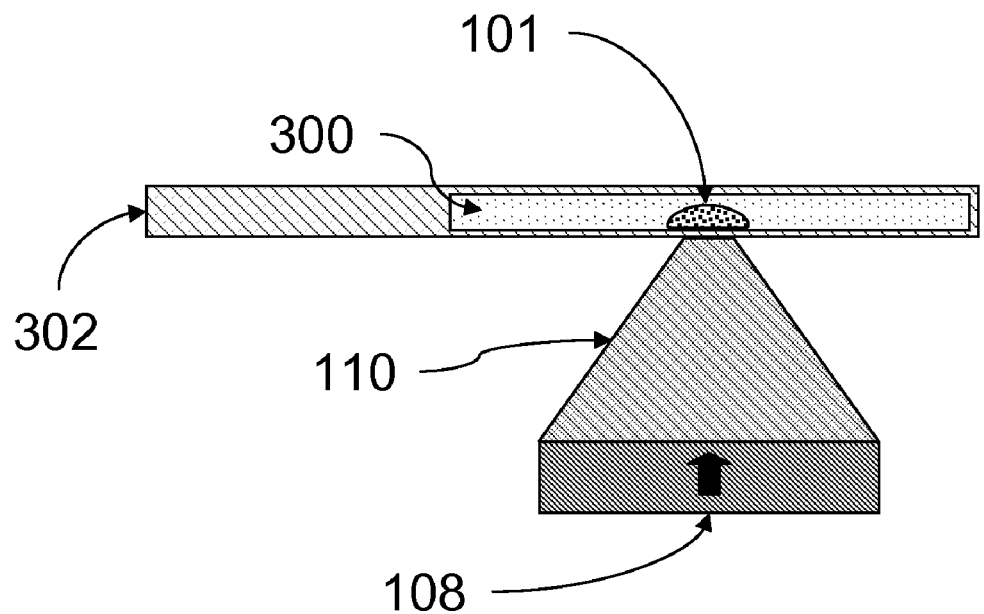
FIGS. 3a and 3b show a cross-sectional view and a top view, respectively, of an embodiment of the sample chamber of the present invention.
Figure 3B:
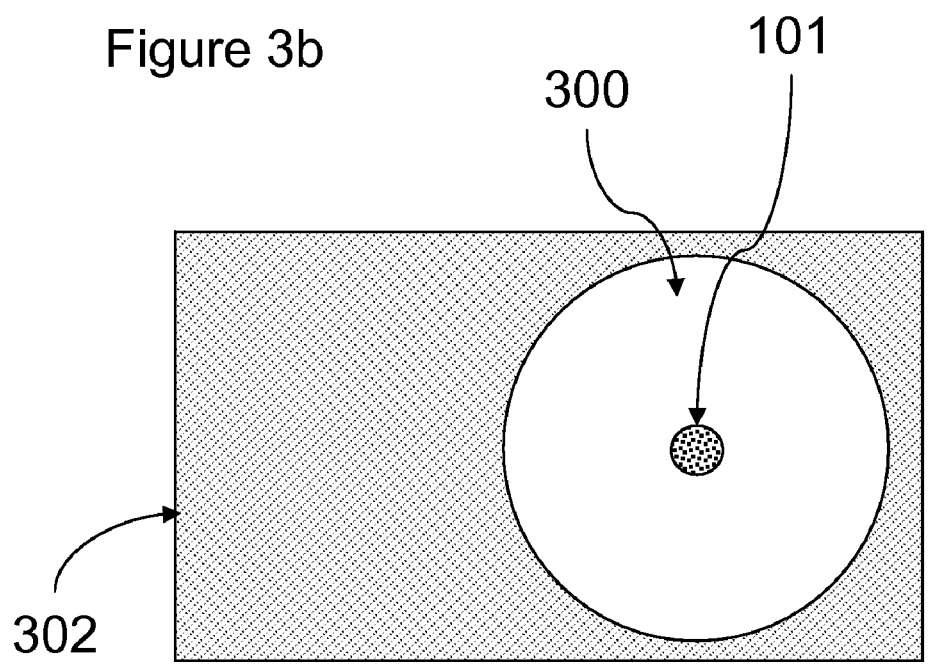

FIGS. 3a and 3b show a cross-sectional view and a top view, respectively, of an alternative embodiment of the sample holder of the invention. Sample holder 302 contains sample chamber 300, formed as a cavity within the sample holder. A sample entry port and a gas exit port (not shown) connect sample chamber 300 with the outside of sample holder 302 to facilitate filling the enclosed chamber with sample fluid. As shown, the enclosed chamber 300 is disc-shaped, i.e., circular with a small depth. However, other shapes may be used. The use of an enclosed sample chamber of a defined volume enables providing a sample of a predetermined volume by simply filling the chamber.

As shown in FIG. 3a, the focusing magnet consisting of magnet 108 and magnet pole piece 110 is positioned underneath the center of the disc-shaped sample chamber 300 to concentrate the analyte-bound particles into pellet 101 in the center of the sample chamber. By positioning the focusing magnet in the center of a round sample chamber, the distance from the edge of the chamber to the detection region is uniform in all directions, which facilitates concentrating the magnetic particles into the pellet 101 evenly from all regions of the sample chamber.

As shown, the sample holder 302 is rectangular to facilitate manipulation of the sample holder and to facilitate holding the sample holder in the instrument. However, the shape and size of the sample holder is not a critical aspect of the invention.

The depth of sample chamber 300 preferably is a shallow as practical without interfering with the concentration of the analyte-bound magnetic particles. For the concentration of lymphocytes using magnetic particles conjugated to antibodies that bind to a cell-surface antigen, the depth of the chamber preferably is about 50 µm. The shallow depth of the sample chamber minimized the amount of sample fluid in the optical path between the pellet 101 of analyte-bound particles and the detector, which minimizes the amount of background signal, thus improving the signal-to-noise ratio obtainable.

The sample chamber can be made from any suitable material, such as glass or plastic. In a preferred embodiment, the sample chamber is made from plastic, such as polystyrene, and has a clear (transparent) top to enable optical detection, and black sides and bottom to minimize ambient or scattered light from interfering with the detection.

FIG. 4

Figure 4:
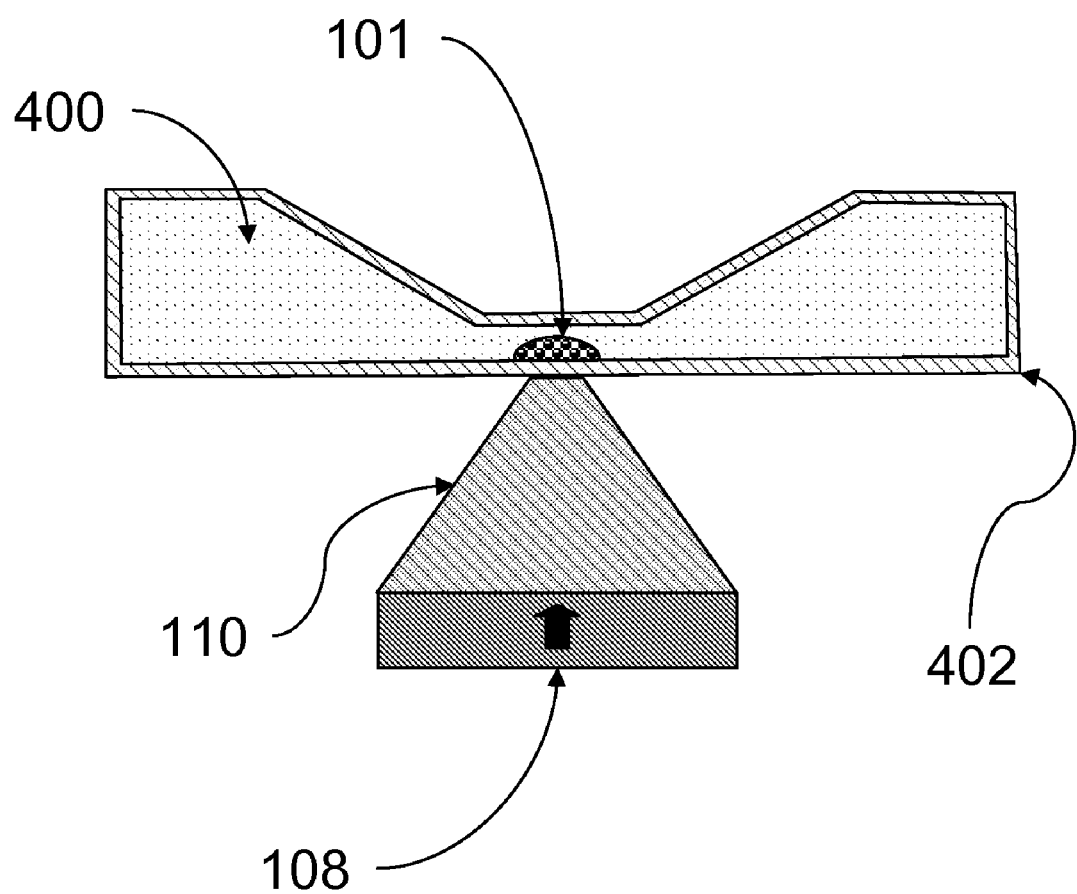
FIG. 4 shows cross-sectional view of an alternative embodiment of the sample chamber of the present invention.

FIG. 4 shows a cross-sectional view of an alternative embodiment of the sample chamber of the present invention. Sample holder 402 contains sample chamber 400, formed as a cavity within the sample holder. A sample entry port and a gas exit port (not shown) connect sample chamber 400 with the outside of sample holder 402 to facilitate filling the enclosed chamber with sample fluid. In this embodiment, the central portion of the top of the sample chamber 400 is recessed such that the depth of the sample chamber in this region is smaller that the depth of the sample chamber in the periphery. As shown, the central portion of sample chamber 400 is positioned over the magnet 108 and magnet pole piece 110, and pellet 101 of analyte-bound magnetic particles is formed in this central area, which corresponds to the detection region. By reducing the depth of a region of the sample chamber corresponding to the detection region, the light path from pellet 101 towards the detection optics (i.e., vertically, as shown in the figure) passes through a minimal amount of sample fluid. For the concentration of lymphocytes using magnetic particles conjugated to antibodies that bind to a cell-surface antigen, the depth of the chamber in the region corresponding to the detection region preferably is about 50 µm.

This embodiment of the sample chamber has several advantages. By minimizing the sample chamber depth in the detection region, the background signal caused by residual sample surrounding pellet 101 is minimized. Furthermore, the use of a greater depth in the periphery of the chamber allows using a larger total sample volume without increasing the diameter of the sample chamber and, consequently, without increasing the distance that the magnet must move the magnetic particles during the concentration step.

As shown in FIG. 4, the central portion of the top of the sample chamber is recessed. However, other shapes of the sample chamber can be used, as long as the concentration of magnetic particles occurs in a detection region having a depth less than the depth elsewhere in the chamber. For example, this detection region can be positioned at an edge of the sample chamber, or can be positioned outside the main sample chamber in a lateral protrusion of the sample chamber. Furthermore, the decrease in sample chamber depth can be achieved either by a recess in the top of the sample chamber, a raised portion in the floor of the sample chamber, or both.

FIG. 5

Figure 5A:
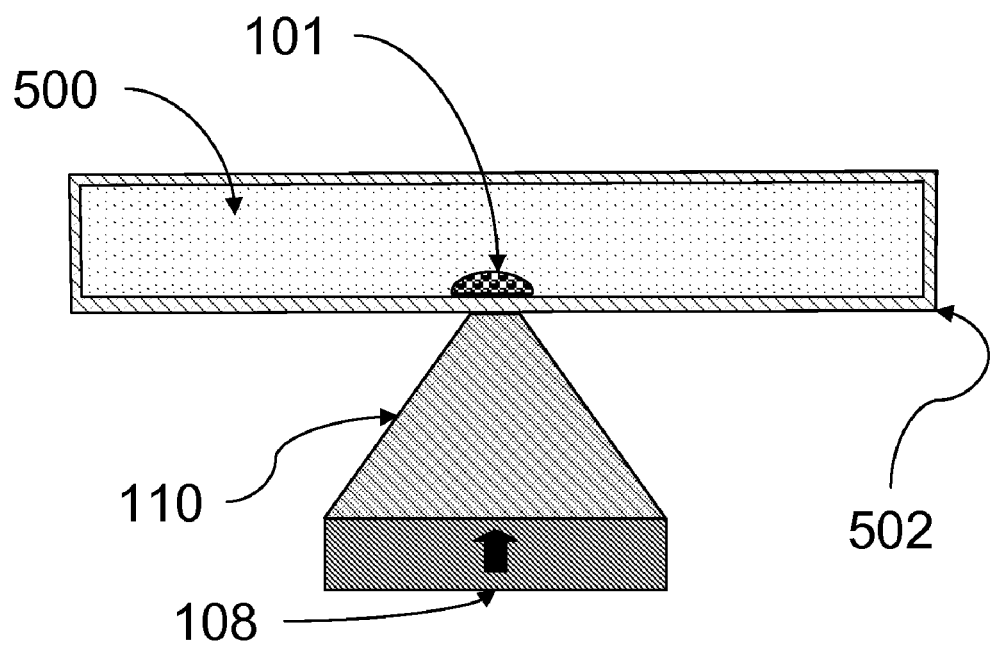
FIGS. 5a and 5b show cross-sectional views an alternative embodiment of the sample chamber of the present invention, before and after compression of the sample chamber.
Figure 5B:
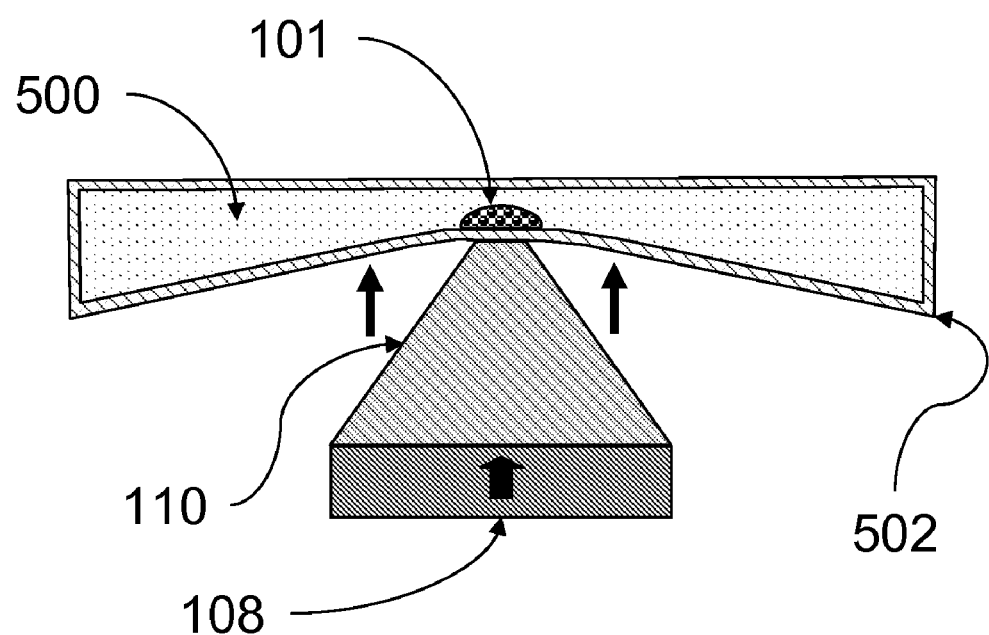

FIGS. 5a and 5b show cross-sectional views of an alternative embodiment of the present invention in which a reduction of depth of the sample chamber in the detection region is achieved after concentration of the analyte-bound magnetic particles by compression of the sample chamber. Enclosed sample chamber 500 is formed as a cavity within sample holder 502. In this embodiment, the bottom surface of the chamber is made of a flexible material. As shown in FIG. 5a, magnetic concentration of the analyte-bound magnetic particles to form pellet 101 is carried out in the uncompressed chamber. As shown in FIG. 5b, after concentration, the focusing magnet consisting of magnet 108 and magnet pole piece 110 is moved relative to the sample chamber to compress the sample chamber in the detection region, thus minimizing the amount of sample fluid present in the optical path prior to detection.

Equivalently, the compression of the sample chamber can be achieved by pressing the top surface of the sample chamber. Either the top surface or the bottom surface of the sample chamber, or both surfaces can be made of a flexible material. Compression can be achieved by raising the magnet pole piece, by lowering the sample chamber, by lowering a structure just above the sample chamber, or by any other method that achieves compression of the sample chamber around the detection region.

Figure 6:
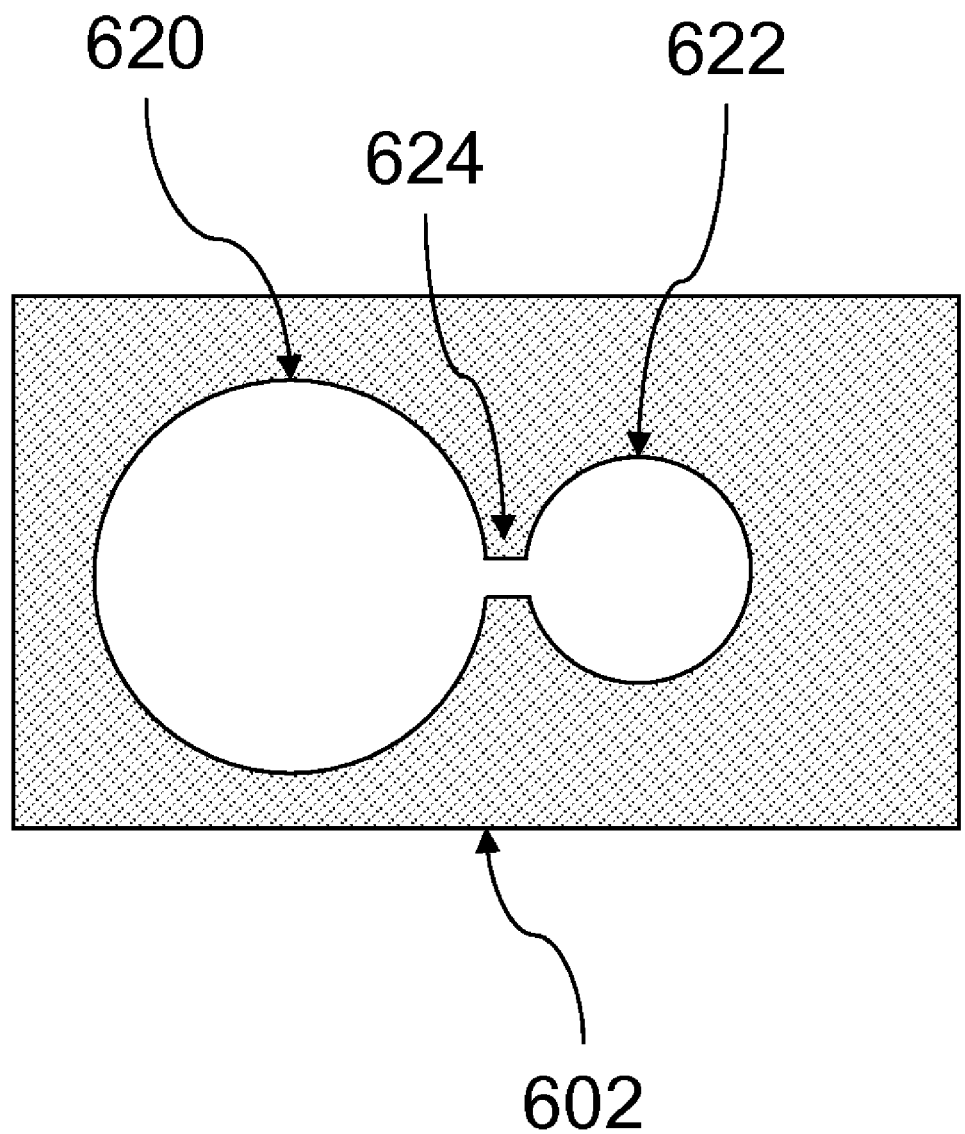
FIG. 6 shows a top view of a two-chambered embodiment of the sample chamber of the present invention.

FIGS. 6 and 7

FIGS. 6 and 7 show an alternative embodiment of the invention in which after the analyte-bound magnetic particles are concentrated into a pellet, the pellet is moved from the sample chamber into a separate detection region or chamber by moving the concentrating magnet relative to the sample chamber. Movement of the particle pellet is achieved by moving the magnet laterally with respect to the sample chamber, either by moving the magnet, or by moving the chamber, or both. The detection chamber contains a detection fluid, preferably an optically clear, non-fluorescent fluid that is immiscible with the sample fluid. Movement of the particle pellet out of the sample chamber into the detection chamber positions the pellet in an optically clear, non-fluorescent fluid environment and, thereby, reduces the background signal.

FIG. 6 shows a top view of a sample chamber holder 602 that contains a sample chamber 620 connected through channel 624 to detection chamber 622. The width of channel 624 is sufficient to enable passage of the pellet of concentrated magnetic particles through the channel. Detection chamber 622 is filled with a detection fluid, preferably an optically clear, non-fluorescent fluid that is immiscible with the sample fluid. For example, the detection fluid can be a clear oil, such as mineral oil or the like. Chamber 620 is filled with sample fluid. The sample fluid and detection fluid remain unmixed and in their respective chambers due to the immiscibility of the fluids and the restricted channel connecting the chambers.

Figure 7A:
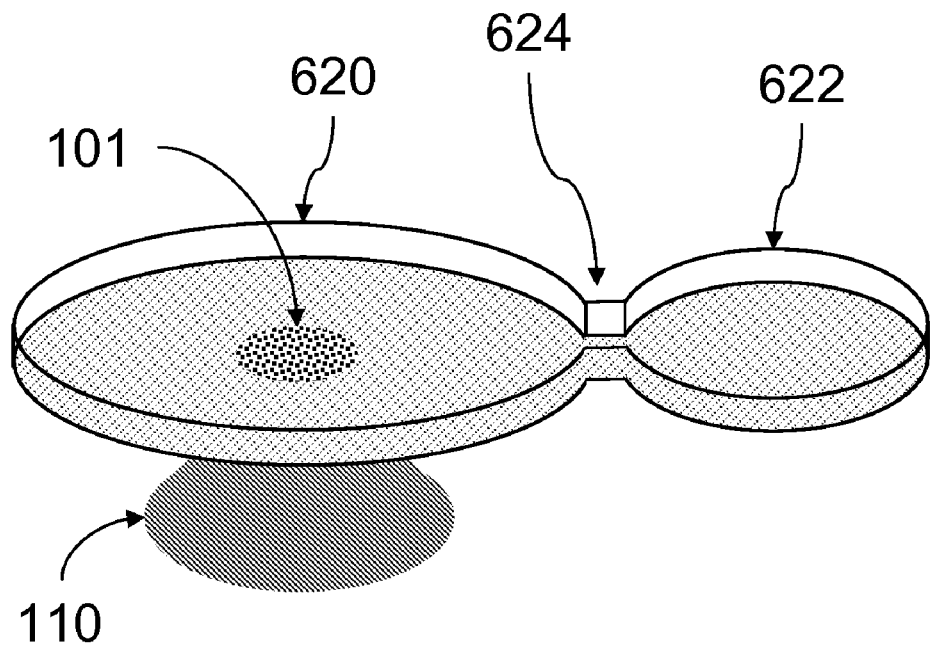
FIGS. 7a and 7b show top, angled views of a two-chambered embodiment of the sample chamber of the present invention, as used in the present methods.
Figure 7B:
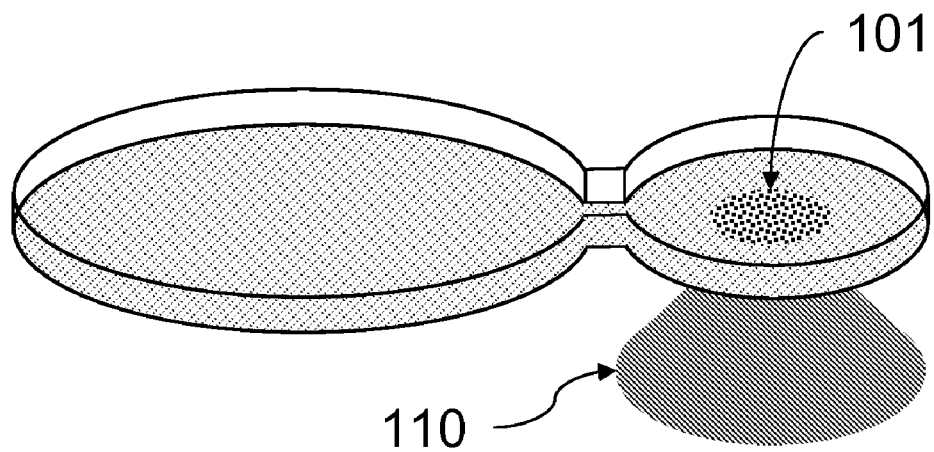

FIGS. 7a and 7b show a top-angled view of the sample chamber of FIG. 6 as used in the present methods. In FIG. 7a, the magnet pole piece 110 is located underneath the sample chamber 620, and the analyte-bound magnetic particles are concentrated into a pellet 101, positioned above the pole. After concentration, the location of the magnetic pole is moved along the bottom of the sample chamber through channel 624 and into detection chamber 622. FIG. 7b shows the final position of the magnet pole underneath detection chamber 622, with pellet 101 of analyte-bound particles now in the detection chamber.

FIG. 8

Figure 8:
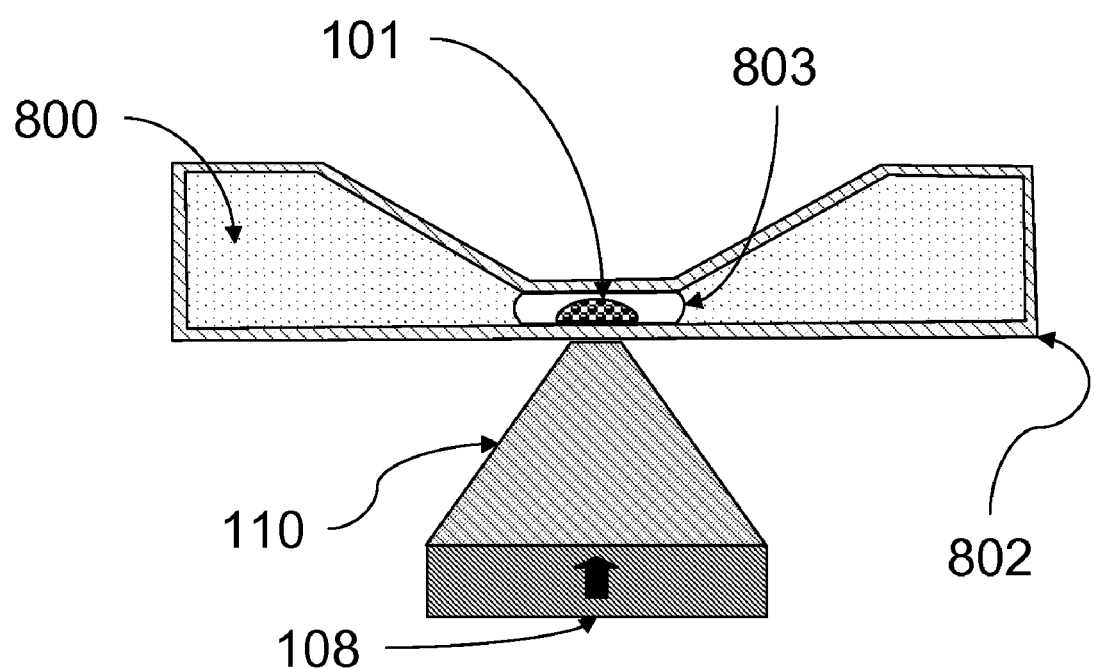
FIG. 8 shows cross-sectional view of an alternative embodiment of the sample chamber of the present invention.

FIG. 8 shows a cross-sectional view of an alternative embodiment of the sample chamber of the present invention. Enclosed sample chamber 800 is formed as a cavity within sample holder 802. In this embodiment, a droplet 803 of optically clear detection fluid that is immiscible in sample fluid is located within the sample chamber in the region corresponding to the detection region. The droplet of detection fluid can be held in place by capillary action or by the surface properties of the sample holder, e.g., by making the inner surface of the detection region of the sample chamber hydrophobic to hold an oil detection fluid. Alternatively, the droplet of detection fluid can be held in place by partial partition or septa, formed in the upper surface of the chamber so as not to interfere with the movement of particles into the detection region.

Sample fluid is added to the sample chamber 800 to fill the region surrounding the droplet of detection fluid. Then, magnetic concentration of the analyte-bound magnetic particles to form pellet 101 is carried out using the focus magnet consisting of magnet 108 and pole piece 110 positioned below droplet of detection fluid in the detection region of the sample chamber. Movement of the particles into the detection region over the magnetic pole 110 results in the pellet 101 being formed inside droplet 803.

FIG. 9

Figure 9A:
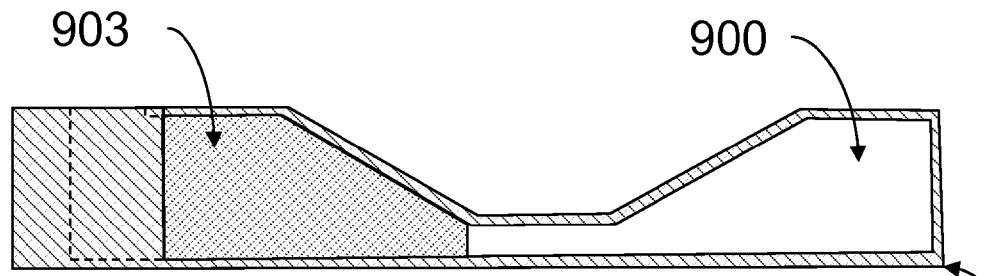
FIGS. 9a and 9b show a cross-sectional view and a top view, respectively, of an alternative embodiment of the sample chamber of the present invention.
Figure 9B:
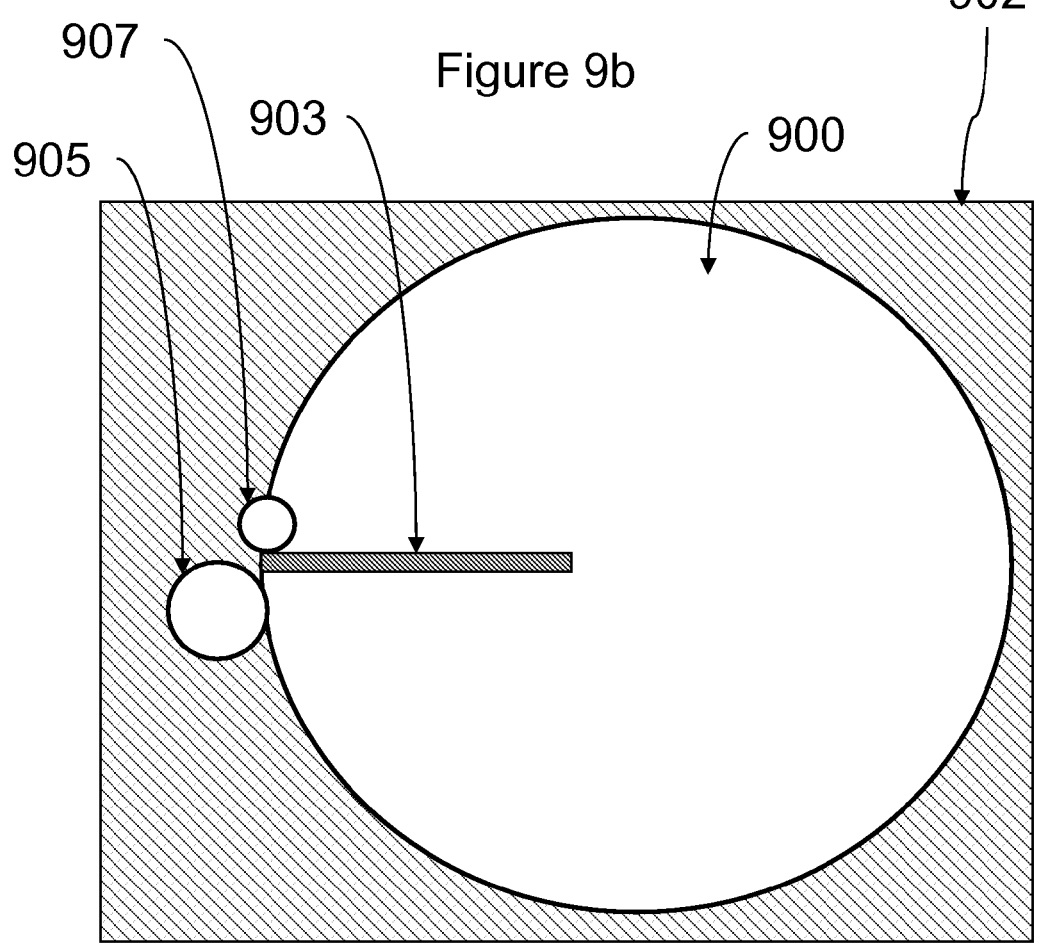

FIGS. 9a and 9b show a cross-sectional view and a top view, respectively, of an alternative embodiment of the sample chamber shown in FIG. 4. Sample holder 902 contains sample chamber 900 with a recessed portion in top of the sample chamber over the detection region. A sample entry port 905 and a gas exit port 907 connect sample chamber 900 with the outside of sample holder 902 to facilitate filling the enclosed chamber with sample fluid. The sample entry port 905 and gas exit port 907 are located on the periphery of the sample chamber adjacent to each other. The sample chamber includes septum 903 from the periphery of the chamber between the sample entry port and the gas exit port to about the periphery of the detection region, such that fluid cannot travel directly from the sample entry port to the gas exit port. The septum facilitates filing of the sample chamber with sample fluid by directing sample fluid around the periphery of the chamber, which lessens the chance of trapping an air bubble in the chamber. Additionally, the septum provides structural support for the upper surface of the chamber, stabilizing its position and the depth of the detection region.

FIG. 10

Figure 10A:
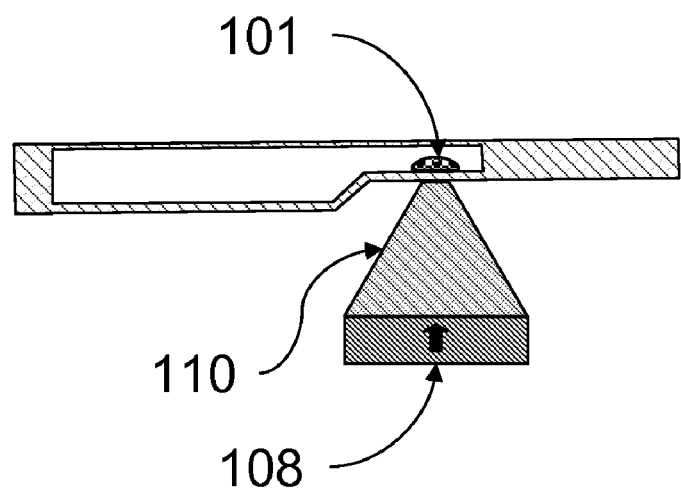
FIGS. 10a and 10b show a cross-sectional view and a top view, respectively, of an alternative embodiment of the sample chamber of the present invention.
Figure 10B:
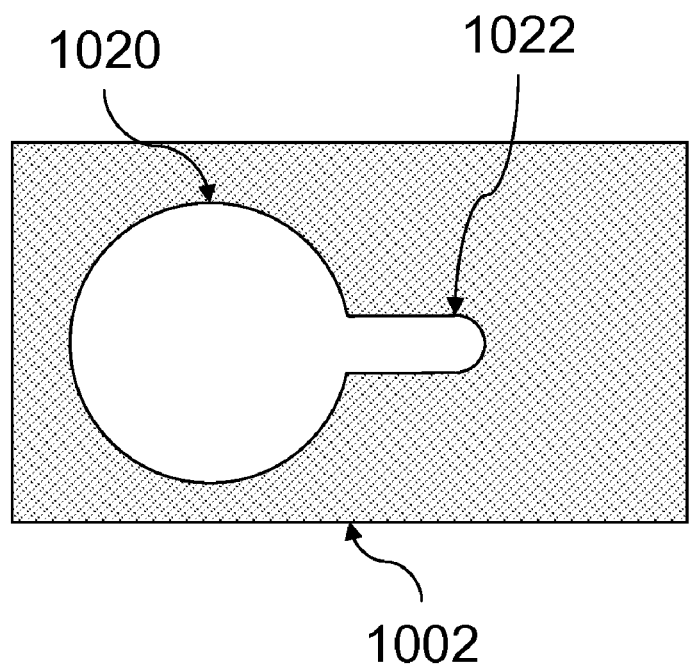

FIGS. 10a and 10b show cross-sectional views of an alternative embodiment of the present invention in which the analyte-bound magnetic particles from the entire sample chamber are concentrated into a detection region at the periphery of the main sample chamber. Enclosed sample chamber 1020, formed as a cavity within sample holder 1002, contains a detection region 1022 having reduced depth that projects out from the main sample chamber. Concentration of the analyte-bound magnetic particles from the entire sample chamber is achieved using the focusing magnet consisting of magnet 108 and magnet pole piece 110 positioned under the detection region. The shallow depth of the detection region minimized the amount of sample fluid present in the optical path.

It was observed that, using a rare earth focusing magnet, concentration of magnetic particles in a liquid sample can occur over distances greater than 1 cm. In preferred embodiments of the present invention, the sample chamber will hold on the order of 10-100 µl and the diameter of the chamber will be less than 1 cm. The field generated by the focusing magnet typically will be strong enough to concentrate the analyte-bound magnetic particles from the entire sample chamber into the detection region positioned at the periphery of the sample chamber using a statically placed focusing magnet.

EXAMPLES

Example 1

CD4$^+$ T Cell Concentration Assay: Antibody Labeling

Instrument

Figure 11:
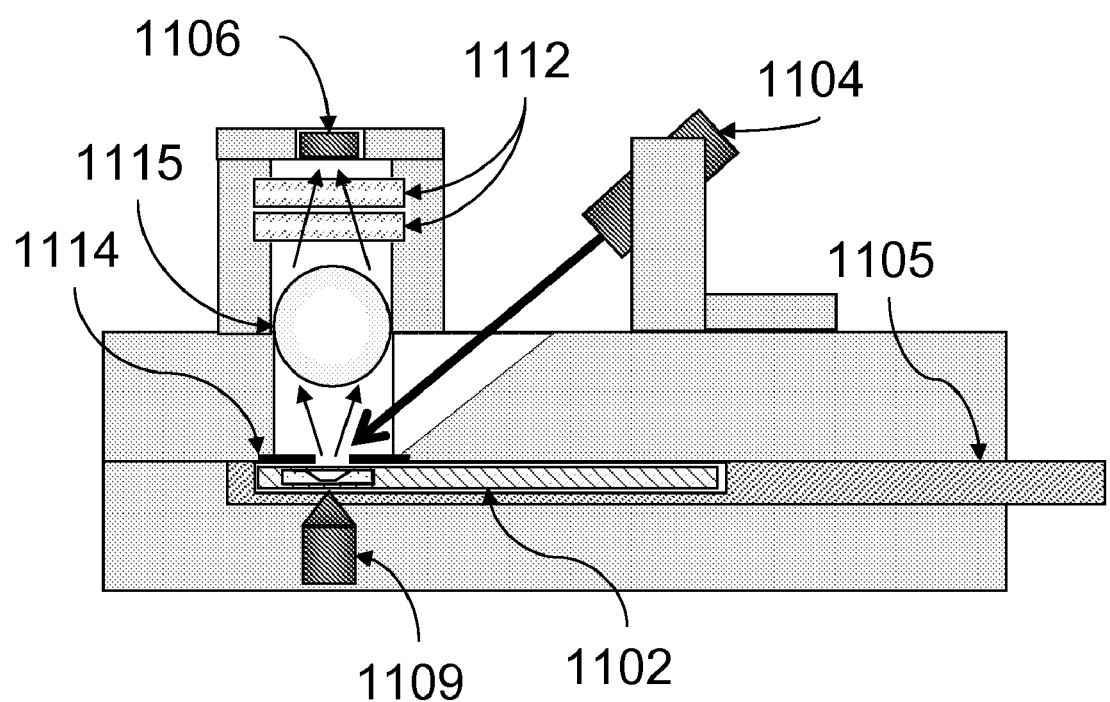
FIG. 11 shows an alternative embodiment of the instrument of the present invention, as described in example 1.

Assays were carried out using an instrument essentially as shown in FIG. 11.

A rectangular sample holder 1102 containing a sample chamber essentially as shown in FIG. 4 was used. The diameter of the sample chamber was about 7 mm, and the total volume of the sample chamber was about 20 µl. The detection region was a region about 2 mm in diameter in the center of the sample chamber. The upper surface of the sample chamber was recessed about 700 µm below the upper surface over the perimeter of the sample chamber such that the depth of the sample chamber in the detection region was about 50 µm. The sample holder was carried in a sample holder carrier 1105, which facilitated inserting the sample chamber into the instrument and shielded the sample chamber from ambient light. Once inserted, the sample chamber was position directly over the focusing magnet 1109.

The focusing magnet consisted of a cylindrical (disc) magnet with an iron cone positioned top of the magnet. The magnet was a samarium cobalt, 3700 gauss magnet 0.25 inches in diameter and 0.2 inches in depth, from Edmunds Optics (Barrington, N.J.). An iron cone having a base diameter of 0.25 inches and a height of 0.175 inches was position on top of the magnet.

The excitation light was from a 650 nm, 5 mW laser diode 1104 positioned to project a beam onto the sample chamber.

A photodiode 1106 detector was positioned above the sample chamber to detect light emitted from the detection region. The output voltage from the photodiode was amplified and displayed on a digital voltmeter (not shown).

A pin-hole aperture 1114 was positioned over the sample detection region to limit the region exposed to the excitation light and to minimize the light detected from outside the detection region. The aperture was a 1.8 mm×2.7 mm oval hole in a thin copper strip, 0.15 mm thick, with the long axis of the oval aligned with the photodiode and the laser to allow for illumination of the sample by the laser beam entering at a 45 degree angle.

An acrylic ball 1115, ⅝" in diameter, was positioned over the pinhole to focus the emitted light towards the photodiode. Two 695 nm long-pass filters 1112 were positioned between the ball and the photodiode to filter out scattered excitation light. The filters, each 12 mm×12 mm, were cut from a commercially available 2"×2" filter (Edmund Optics, Barrington, N.J.).

Reagents

Commercially available CD4 antibody-coated magnetic particles (BD Imag™ beads, BD Biosciences, San Jose, Calif.) were used as magnetic capture reagents.

Commercially available CD3 antibodies conjugated to APC (BD Bioscience, San Jose, Calif.) were used as detection reagents.

Standard Samples

In order to generate a standard curve correlating measured fluorescence with the concentration of CD4$^+$ T cells, a series of whole blood samples were created, each containing a known concentration of CD4$^+$ T cells. The series of standard samples were created to encompass a medically significant range of CD4$^+$ T cell concentrations. The series of whole blood samples containing known concentrations of CD4$^+$ T cells were created by mixing various proportions of first sample of whole blood in which the CD4$^+$ T cells had been independently measured and a second sample of whole blood in which the CD4$^+$ T cells had been removed. The concentration of CD4$^+$ T cells in the first whole blood sample from a healthy individual (i.e., normal CD4 count) was measured by flow cytometry using BD Tritest™ reagents on a BD FACS-Calibur™ flow cytometer (BD Biosciences, San Jose, Calif.). The second, CD4$^+$ T cell-depleted whole blood sample was created by magnetically separating CD4$^+$ T cells from whole blood using BD Imag™ beads (BD Biosciences, San Jose, Calif.), essentially following the product instructions. By combining portions of the whole blood sample containing a known concentration of CD4$^+$ T cells and the sample of CD4$^+$ T cell-depleted whole blood, a series of whole blood samples were created containing from 0 to 600 CD4$^+$ T cells per µl of blood, in intervals of 100.

Assay

For each assay, 100 μL of whole blood were combined with 20 μg of CD4 antibody-coated magnetic particles (capture reagent) and 5 μL of 5 μg/mL of APC-labeled CD3 antibodies (detection reagent) and incubated at room temperature for 30 minutes with agitation to allow for binding of the reagents to the cells. Then, 20 μL of the mixture was transferred to the sample chamber. The sample chamber was inserted into the instrument such that the focusing magnet was positioned directly underneath the detection region, and magnetic concentration was allowed to proceed for one minute. Following concentration, the emission from the concentrated, labeled cells was measured.

As noted above, the output voltage from the photodiode was amplified and displayed on a digital voltmeter. Although this output voltage corresponds to the amount of fluorescence emission measured, the numerical value reported depends on various instrument-dependent factors, such as the sensitivity and efficiency of the photodiode and the amount of signal amplification. For a given instrument, the measured output voltage provides a relative measure of the relative fluorescence emission from different samples, and is herein reported as measured in relative fluorescence units (RFU).

Standard Curve

Figure 12:
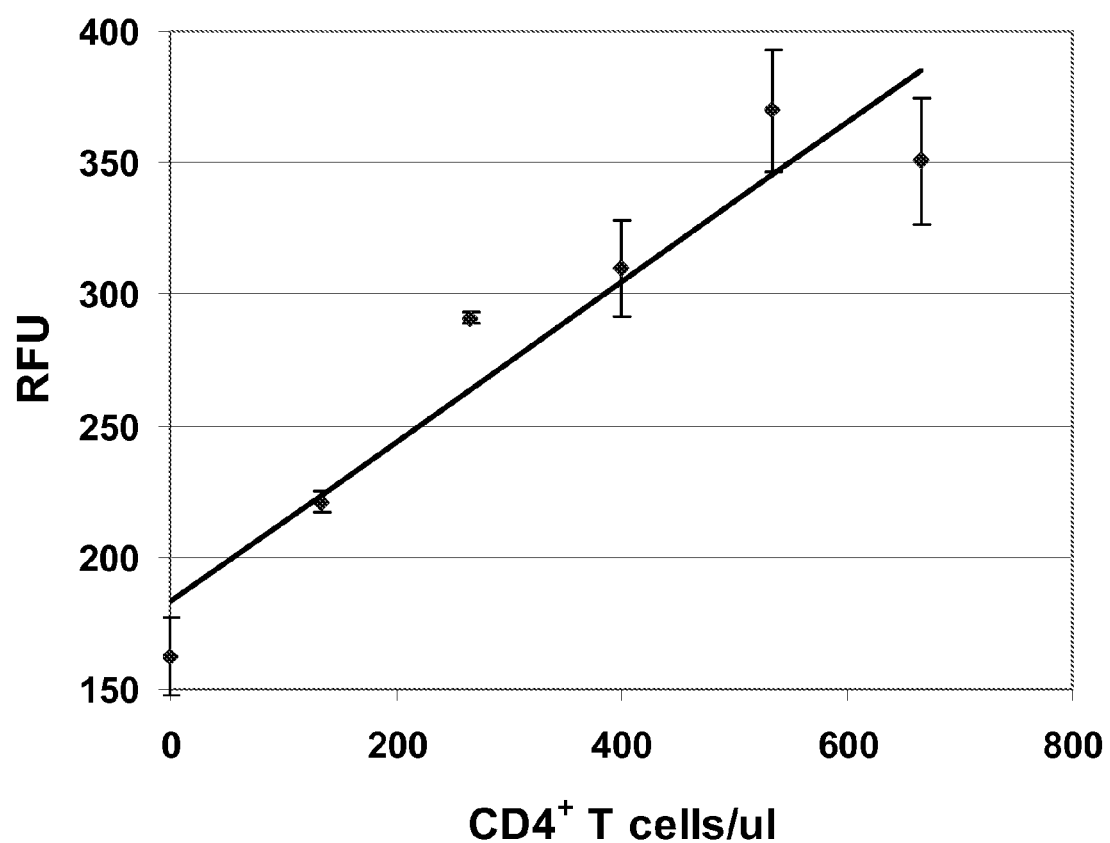
FIG. 12 shows the results the assay described in example 1.

Assays were carried out using each of the standard samples, described above. Assays of each sample were carried out in triplicate. The average and standard deviation (SD) of the fluorescence measurements from each sample (RFU) are provided in table 1, below, and in FIG. 12. In FIG. 12, the error bars shown are ±1 SD.

TABLE 1

| | Total Fluorescence (RFU) | | | | |
|---|---|---|---|---|---|
| $CD4^+$ T cells/μl | Replicate 1 | Replicate 2 | Replicate 3 | mean | SD |
| 0 | 194 | 151 | 172 | 162 | 15 |
| 133 | 266 | 218 | 223 | 221 | 4 |
| 266 | 237 | 292 | 289 | 291 | 2 |
| 400 | 309 | 322 | 297 | 310 | 18 |
| 533 | 268 | 353 | 386 | 370 | 23 |
| 666 | 360 | 368 | 334 | 351 | 24 |

The data show that the measurement of the total fluorescence from labeled, magnetically concentrated $CD4^+$ T cells correlates well with the number of $CD4^+$ T cells in the sample.

A standard curve was generated from the data obtained from the standard samples by fitting the data to the line, $$RFU = C_1 [CD4^+ \, T \, cells] + C_2,$$

where $[CD4^+ \, T \, cells]$ is the concentration of $CD4^+$ T cells, and $C_1$ and $C_2$ are constants obtained from fitting the data to the line. The standard curve is depicted in FIG. 12.

Patient Samples

Samples of whole blood from different four patients were analyzed both using the assay described and by flow cytometry, both as described, above. The concentration of $CD4^+$ T cells in each patient sample was calculated from the measured RFU using the standard curve obtained from standard samples, as follows:

$$[CD4^+ \, T \, cells]_p = (RFU_p - C_2)/C_1,$$

where the subscript p refers to values corresponding to the patient sample. The data are shown in table 2, below.

TABLE 2

| Patient | Number of $CD4^+$ T-cells in 1 μl of blood | |
|---|---|---|
| Sample ID | Flow cytometry | $CD4^+$ T cell concentration assay: antibody labeling |
| 930 | 578 | 619 |
| 3090 | 439 | 461 |
| 4090 | 352 | 381 |
| 5035 | 463 | 281 |

The data show that the measurements of the concentration of $CD4^+$ T cells in the patient samples correlated well with the measurement carried out using flow cytometry.

Example 2

$CD4^+$ T Cell Concentration Assay: DNA-Dye Labeling

This example describes the use of a nucleic acid stain to fluorescently label all cells in the sample. The instrument and assay methods were essentially as described in example 1, with the exception of the changes described, below.

Reagents

Commercially available CD4 antibody-coated magnetic particles (BD Imag™ beads, BD Biosciences, San Jose, Calif.) were used as magnetic capture reagents, as described in example 1.

A permeant DNA-binding dye, DRAQ5 (Biostatus Ltd., Leicestershire, England) was used as a detection reagent. Use of this dye results in the labeling of all nucleated cells in the blood sample.

Assay

Sample of whole blood were pretreated to selectively remove monocytes. Removal of monocytes was carried by magnetic depletion using CD14 antibody-coated magnetic particles (BD Imag™ beads, BD Biosciences, San Jose, Calif.) following the manufacturer's instructions.

For each assay, 100 μL of whole blood were combined with 20 μg of CD4 antibody-coated magnetic particles (capture reagent) and 10 μL of 50 μmolar DRAQ-5 (detection reagent) and incubated at room temperature for 30 minutes with agitation to allow for binding of the reagents to the cells. Then, 10 μl of the stained sample was diluted with 10 μL of buffer (PBS, 0.1 g/l TWEEN™ 20 [polyoxyethylene(20)sorbitan-monolaurate], 0.1% sodium azide, 1.5% Fetal Bovine Serum, pH 7.4), and the resulting 20 μl sample was transferred to the sample chamber. The sample chamber was inserted into the instrument such that the focusing magnet was positioned directly underneath the detection region, and magnetic concentration was allowed to proceed for one minute. Following concentration, the output of the photodetector was measured and reported as RFU.

Standard Curve

Figure 13:
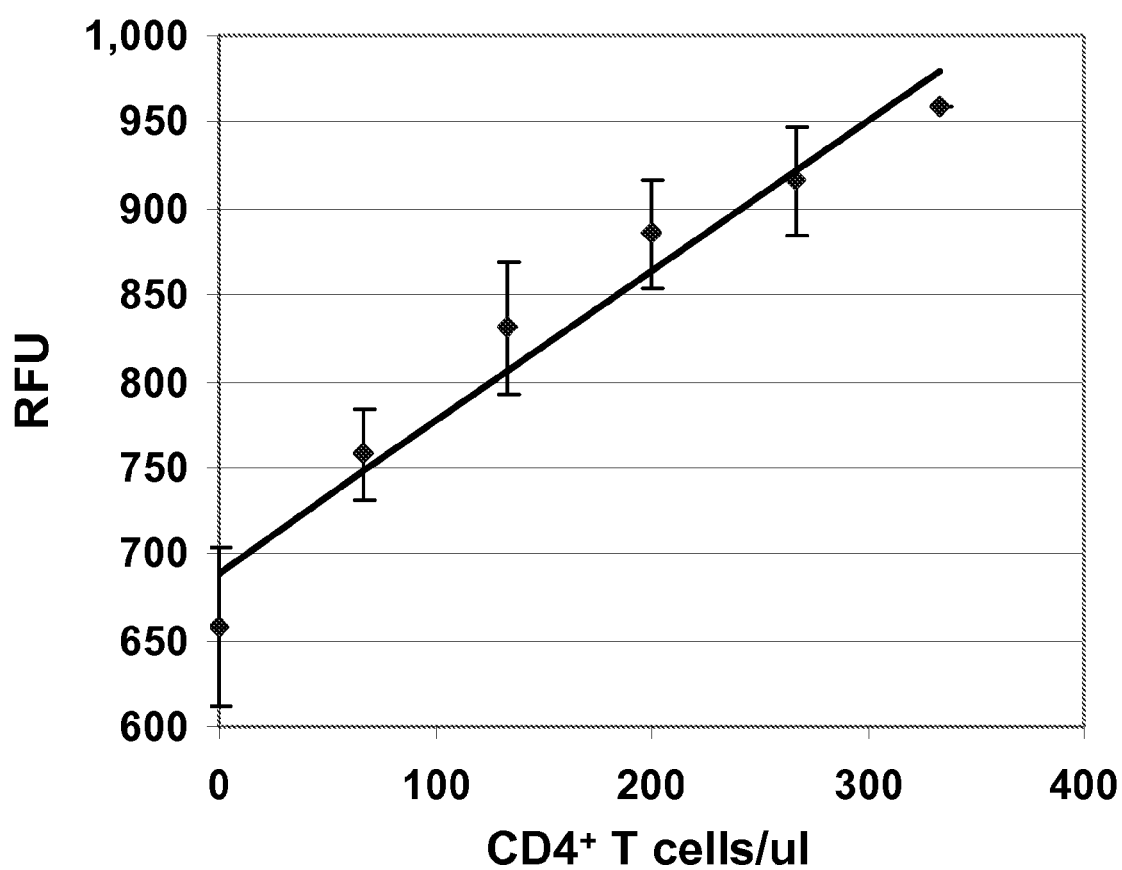
FIG. 13 shows the results the assay described in example 2.

Assays were carried out using each of the standard samples, described above. Assays were carried out in duplicate. Because of the dilution step included in sample preparation, the number of cells per μl in each standard assay is half that of the corresponding assay described in example 1. The average and standard deviation (SD) of the fluorescence measurements from each sample (RFU) are provided in table 3, below, and in FIG. 13. In FIG. 13, the error bars shown are ±1 SD.

TABLE 3

| CD4+ T | Total Fluorescence (RFU) | | | |
|---|---|---|---|---|
| cells/uL | Replicate 1 | Replicate 2 | Average | SD |
| 0 | 626 | 690 | 658 | 45 |
| 67 | 739 | 776 | 758 | 26 |
| 133 | 858 | 804 | 831 | 38 |
| 200 | 908 | 863 | 886 | 32 |
| 266 | 938 | 894 | 916 | 31 |
| 333 | 959 | (not recorded) | 959 | 0 |

The data show that the measurement of the total fluorescence from labeled, magnetically concentrated CD4+ T cells correlates well with the number of CD4+ T cells in the sample.

A standard curve was generated from the data obtained from the standard samples by fitting the data to the line, as described above. The standard curve is depicted in FIG. 13.

Patient Samples

Samples of whole blood from four different patients were analyzed both using the assay described and by flow cytometry, both as described, above. The concentration of CD4+ T cells in each patient sample was calculated from the measured RFU using the standard curve obtained from standard samples, as described, above. The data are shown in table 4, below.

TABLE 4

| | Number of CD4+ T-cells in 1 μl of blood | |
|---|---|---|
| Sample ID | Flow cytometry | CD4+ T cell concentration assay: DNA-dye labeling |
| 930 | 578 | 438 |
| 3090 | 439 | 316 |
| 4090 | 352 | 293 |
| 5035 | 463 | 303 |

The data show that the measurements of the concentration of CD4+ T cells in the patient samples correlated well with the measurement carried out using flow cytometry.

We claim:

1. An optical instrument for the analysis of an analyte contained in a fluid sample, comprising:
    A sample holder containing a sample chamber having a volume of less than about 100 μl and containing a detection region having a vertical depth of less than about 100 μm wherein said top surface said chamber over said detection region is optically clear, and wherein the depth of the sample chamber in said detection region is less than the depth of the sample chamber outside the detection region;
    A focusing magnet having a tapered pole piece, wherein said pole piece is tapered to less that about 100 μm; wherein said focusing magnet is position below said detection region of said sample chamber;
    An excitation light source adapted to illuminate said detection region through said optically clear top surface of said sample chamber over said detection region;
    Detection optics adapted to detect light emitted from said detection region through said optically clear top surface of said sample chamber over said detection region and produce a signal corresponding to the amount of light detected.

2. The instrument of claim 1 wherein said focusing magnet consists of a permanent magnet and a conical or frustum-shaped cone made from a soft-magnetic material.

3. The instrument of claim 1 wherein said the top surface of said sample chamber has a depression over said detection region such that the depth of said sample chamber in said detection region is less than the depth of the sample chamber outside the detection region.

4. The instrument of claim 1 wherein said detection optics contains a photodiode adapted to detect light emitted from said detection region through said optically clear top surface of said sample chamber over said detection region.

5. The instrument of claim 1, further comprising an aperture interposed between said sample chamber and said detection optics to block light emitted from sample chamber outside said detection region from entering said detection optics.

6. The instrument of claim 1, wherein said sample chamber further comprises a septum adapted to direct the flow of sample introduced into said chamber.

7. The instrument of claim 1, wherein said sample chamber further comprises a drop of a detection fluid, wherein said detection fluid is optically clear and immiscible in said fluid sample, and wherein said drop is positioned in said detection region.

8. The instrument of claim 1, wherein said sample chamber further comprises a drop of a detection fluid, wherein said detection fluid is optically clear and immiscible in said fluid sample, and wherein said drop is positioned in said detection region.

* * * * *